(12) United States Patent
Kimura

(10) Patent No.: US 12,327,353 B2
(45) Date of Patent: Jun. 10, 2025

(54) IMAGE SELECTION SUPPORT DEVICE, IMAGE SELECTION SUPPORT METHOD, AND IMAGE SELECTION SUPPORT PROGRAM

(71) Applicant: FUJIFILM Corporation, Tokyo (JP)

(72) Inventor: Yuya Kimura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 351 days.

(21) Appl. No.: 17/823,852

(22) Filed: Aug. 31, 2022

(65) Prior Publication Data

US 2022/0414873 A1 Dec. 29, 2022

Related U.S. Application Data

(63) Continuation of application No. PCT/JP2021/000926, filed on Jan. 13, 2021.

(30) Foreign Application Priority Data

Mar. 3, 2020 (JP) ................................ 2020-036270

(51) Int. Cl.
*G06T 7/00* (2017.01)
*G06F 3/04842* (2022.01)

(52) U.S. Cl.
CPC ........ *G06T 7/0012* (2013.01); *G06F 3/04842* (2013.01); *G06F 2203/04803* (2013.01); *G06T 2200/24* (2013.01); *G06T 2207/10068* (2013.01); *G06T 2207/10152* (2013.01); *G06T 2207/30096* (2013.01)

(58) Field of Classification Search
CPC .............. G06T 7/0012; G06T 2200/24; G06T 2207/10068; G06T 2207/10152;
(Continued)

(56) References Cited

U.S. PATENT DOCUMENTS

| 2017/0085831 A1 | 3/2017 | Hashimoto et al. |
| 2020/0170484 A1 | 6/2020 | Kamon |
| 2020/0170485 A1 | 6/2020 | Takahashi et al. |
| 2020/0305700 A1 | 10/2020 | Kamon |

FOREIGN PATENT DOCUMENTS

| JP | H10-323326 A | 12/1998 |
| JP | 2008-062069 A | 3/2008 |

(Continued)

OTHER PUBLICATIONS

Machine translation for JP 2014-018471, IDS (Year: 2014).*

(Continued)

*Primary Examiner* — Qian Yang
(74) *Attorney, Agent, or Firm* — Studebaker Brackett PLLC

(57) ABSTRACT

An image selection support device supports the selection of a still image based on captured image data obtained by an endoscope. By using a first still image acquired based on the captured image data at a time when an operator of the endoscope performs an acquisition operation of the still image, and one or more second still images acquired from the captured image data at a time different from the time when the acquisition operation is performed, the image selection support device extracts a third still image having an imaging time point that satisfies a predetermined condition with an imaging time point of the first still image from among the second still images, and associates the first still image with the third still image.

12 Claims, 12 Drawing Sheets

(58) Field of Classification Search
CPC ....... G06T 2207/30096; G06F 3/04842; G06F 2203/04803; G06F 3/0482; G06F 3/04845; G16H 10/60; G16H 15/00; G16H 30/20; G16H 30/40; A61B 1/045
See application file for complete search history.

(56) References Cited

FOREIGN PATENT DOCUMENTS

| | | |
|---|---|---|
| JP | 2013-230319 A | 11/2013 |
| JP | 2014-018471 A | 2/2014 |
| JP | 2016-067782 A | 5/2016 |
| WO | 2016/084779 A1 | 6/2016 |
| WO | 2018/216618 A1 | 11/2018 |
| WO | 2019/039259 A1 | 2/2019 |
| WO | 2019/130964 A1 | 7/2019 |

OTHER PUBLICATIONS

An Office Action; "Notice of Reasons for Refusal," mailed by the Japanese Patent Office on Sep. 12, 2023, which corresponds to Japanese Patent Application No. 2022-505008 and is related to U.S. Appl. No. 17/823,852; with English language translation.
International Search Report issued in PCT/JP2021/000926; mailed Mar. 16, 2021.
Written Opinion of the International Searching Authority issued in PCT/JP2021/000926; mailed Mar. 16, 2021.

* cited by examiner

FIG. 4

| FUJISUKE FUJI | ♂ AB(+) | | RESERVATION DETAILS | | | | | | | | |
|---|---|---|---|---|---|---|---|---|---|---|---|
| 0123456789001234 | 31 YEARS OLD (11.11.1977) INPATIENT ABC BUILDING 301 | | | | | | | | | | |

| RECEPTION | CANCEL | RESERVATION REGISTRATION | RESERVATION EDITING | DELETION | CALL | RELEASE | | ORDER SEARCH LIST | EXAMINATION RECORD | INTERVIEW AND PRETREATMENT | IMAGING REGISTRATION | IMAGE DISPLAY | REPORT | PATHOLOGY | PERFORMANCE | Option |

| VISIT | RECEPTION | EXAMINATION | COUNTING | PATIENT ID | PATIENT NAME | DATE OF BIRTH | AGE | GENDER | ORDER NUMBER | RECEPTION TIME PRINTING | LIST PRINTING | FILE OUTPUT | SCHEDULED DATE | SCHEDULED TIME POINT | INPATIENT/OUTPATIENT CLASSIFICATION | EXAMINATION ITEM |
|---|---|---|---|---|---|---|---|---|---|---|---|---|---|---|---|---|
| ○ | ○ | ○ | | 1234567801234 | FUJISUKE FUJI | 11/11/1977 | 31 | MALE | 111111122222 | | | | 12/11/2008 | 11:30 | INPATIENT | UPPER PART |
| ○ | ○ | ○ | | 1234567801235 | FUJIO FUJI | 12/12/1985 | 23 | MALE | 111111122222 | | | | 12/11/2008 | 12:00 | OUTPATIENT | UPPER PART |
| ○ | | | | 1234567801236 | FUJIO FUJI | 12/12/1985 | 23 | MALE | 111111333322 | | | | 12/13/2008 | 16:40 | OUTPATIENT | LOWER PART |
| ○ | | | | 1234567801237 | FUJIKO FUJI | 12/12/1985 | 23 | FEMALE | 111234561111 | | | | 12/12/2008 | 09:30 | OUTPATIENT | UPPER PART |
| | | | | 1234567801238 | MASAHARU FUJIYAMA | 02/06/1969 | 39 | MALE | 111112345611 | | | | 12/12/2008 | 12:50 | INPATIENT | UPPER PART |
| | | | | 1234567801239 | FUSHIMI FUJI | 12/12/1985 | 23 | FEMALE | 111111143215 | | | | 12/14/2008 | 10:30 | INPATIENT | BRONCHUS |

LOG-IN PARTY: ABCDEFGHIJ    LOG OUT

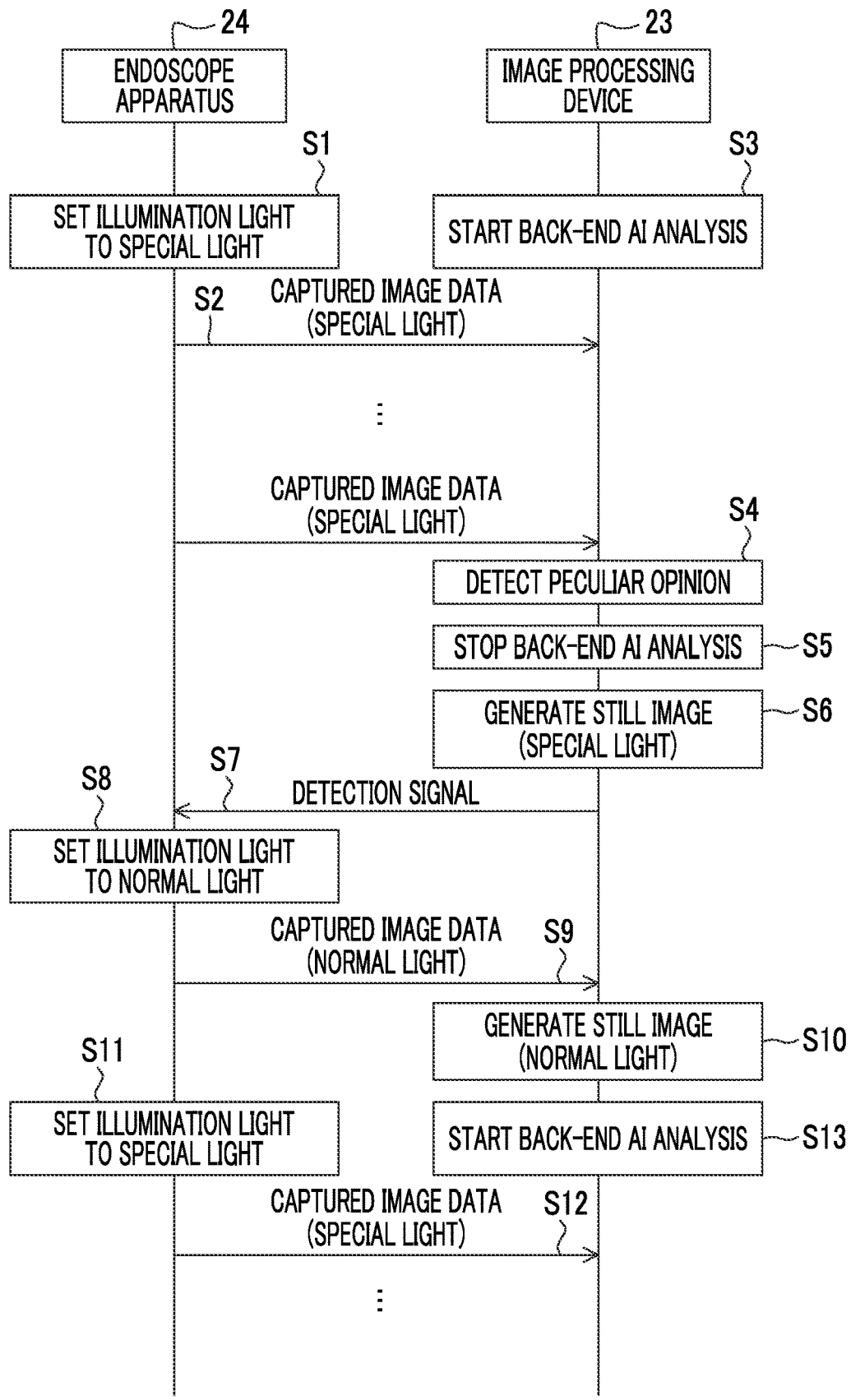

IMAGE SELECTION SUPPORT DEVICE, IMAGE SELECTION SUPPORT METHOD, AND IMAGE SELECTION SUPPORT PROGRAM

CROSS REFERENCE TO RELATED APPLICATION

This is a continuation of International Application No. PCT/JP2021/000926 filed on Jan. 13, 2021, and claims priority from Japanese Patent Application No. 2020-036270 filed on Mar. 3, 2020, the entire disclosures of which are incorporated herein by reference.

BACKGROUND OF THE INVENTION

1. Field of the Invention

The present invention relates to an image selection support device, an image selection support method, and a computer readable medium storing an image selection support program which support selection of an image obtained by imaging with an endoscope.

2. Description of the Related Art

In the related art, an image management system that accumulates images obtained by imaging with an endoscope is known. The images accumulated in the image management system are inserted as a key image, for example, in a report created for an examination by an endoscope.

The image acquisition is manually performed, for example, at a timing when an image acquisition operation by an operator of the endoscope is performed.

Alternatively, the image acquisition is automatically performed without the image acquisition operation by the operator of the endoscope. For example, JP2016-67782A discloses a configuration in which, in order to surely store an optimum image for diagnosis, such as a lesion image, without omission, an index value of a mucous membrane information is calculated from an image signal obtained by imaging an observation target with an endoscope, and a specific image signal that is determined to satisfy a specific condition is automatically stored based on the index value.

SUMMARY OF THE INVENTION

It is desirable that the image used for the key image of the report or the like can be selected from among the manually and automatically acquired images.

For example, in some cases, the manually acquired image is an image, such as an image with a large blur, at an inappropriate timing due to a delay in the acquisition operation of the operator. In addition, in some cases, with only the manually acquired image, a necessary image cannot be obtained due to the operator who forgets the acquisition operation or fails the acquisition operation.

On the other hand, in a case in which the image is automatically acquired, it is difficult to determine a complete standard for automatically acquiring the necessary image. Therefore, in some cases, the automatically acquired image includes an unnecessary image. In addition, in some cases, the necessary image cannot be obtained only with the automatically acquired image.

However, in a case of a configuration in which the image is selected from among the manually and automatically acquired images, it is difficult to select an appropriate image from among these images. For example, it is difficult for an image selector to specify which image is automatically acquired at an imaging time point of the image close to the imaging time point of the manually acquired image and it is difficult to compare these images.

The present invention has been made in view of the above circumstances, and is to provide an image selection support device, an image selection support method, and a computer readable medium storing an image selection support program which enable to easily select an appropriate image from among manually and automatically acquired images.

An aspect of the present invention relates to an image selection support device that supports selection of a still image based on captured image data obtained by an endoscope, the device comprising a processor, and a memory, in which the memory records a first still image acquired based on the captured image data at a time when an operator of the endoscope performs an acquisition operation of a still image, and one or more second still images acquired from the captured image data at a time different from the time when the acquisition operation is performed, and the processor is configured to extract a third still image from among the one or more second still images, an imaging time point of the third still image and an imaging time point of the first still image satisfying a predetermined condition, associate the first still image with the third still image, display the first still image and the third still image on a display in association with each other, and select, as a selected still image, a still image on which a selection operation by a user is performed, from the first still image and the third still image displayed on the display in association with each other.

Another aspect of the present invention relates to an image selection support method of supporting selection of a still image based on captured image data obtained by an endoscope, the method comprising, by using a first still image acquired based on the captured image data at a time when an operator of the endoscope performs an acquisition operation of a still image, and one or more second still images acquired from the captured image data at a time different from the time when the acquisition operation is performed, extracting a third still image from among the one or more second still images, an imaging time point of the third still image and an imaging time point of the first still image satisfying a predetermined condition; associating the first still image with the third still image; displaying the first still image and the third still image on a display in association with each other; and selecting, as a selected still image, a still image on which a selection operation by a user is performed, from the first still image and the third still image displayed on the display in association with each other.

Still another aspect of the present invention relates to a non-transitory computer readable medium storing an image selection support program of supporting selection of a still image based on captured image data obtained by an endoscope, the program causing a computer to execute a process comprising, by using a first still image acquired based on the captured image data at a time when an operator of the endoscope performs an acquisition operation of a still image, and one or more second still images acquired from the captured image data at a time different from the time when the acquisition operation is performed, extracting a third still image from among the one or more second still images, an imaging time point of the third still image and an imaging time point of the first still image satisfying a predetermined condition; associating the first still image with the third still image; displaying the first still image and the third still image on a display in association with each other; and selecting, as a selected still image, a still image on which a selection operation by a user is performed, from the first still image and the third still image displayed on the display in association with each other.

According to the present invention, it is possible to provide the image selection support device, the image selection support method, and the computer readable medium storing the image selection support program which enable to easily select the appropriate image from among the manually and automatically acquired images.

BRIEF DESCRIPTION OF THE DRAWINGS

FIG. 4 is a diagram showing an example of a basic screen of an application of a client PC 22.

FIG. 12 is a sequence diagram showing an example of normal light imaging based on automatic acquisition during special light observation.

DESCRIPTION OF THE PREFERRED EMBODIMENTS

In the following, an embodiment of the present invention will be described with reference to the drawings.

Example of Embodiment

Figure 1:
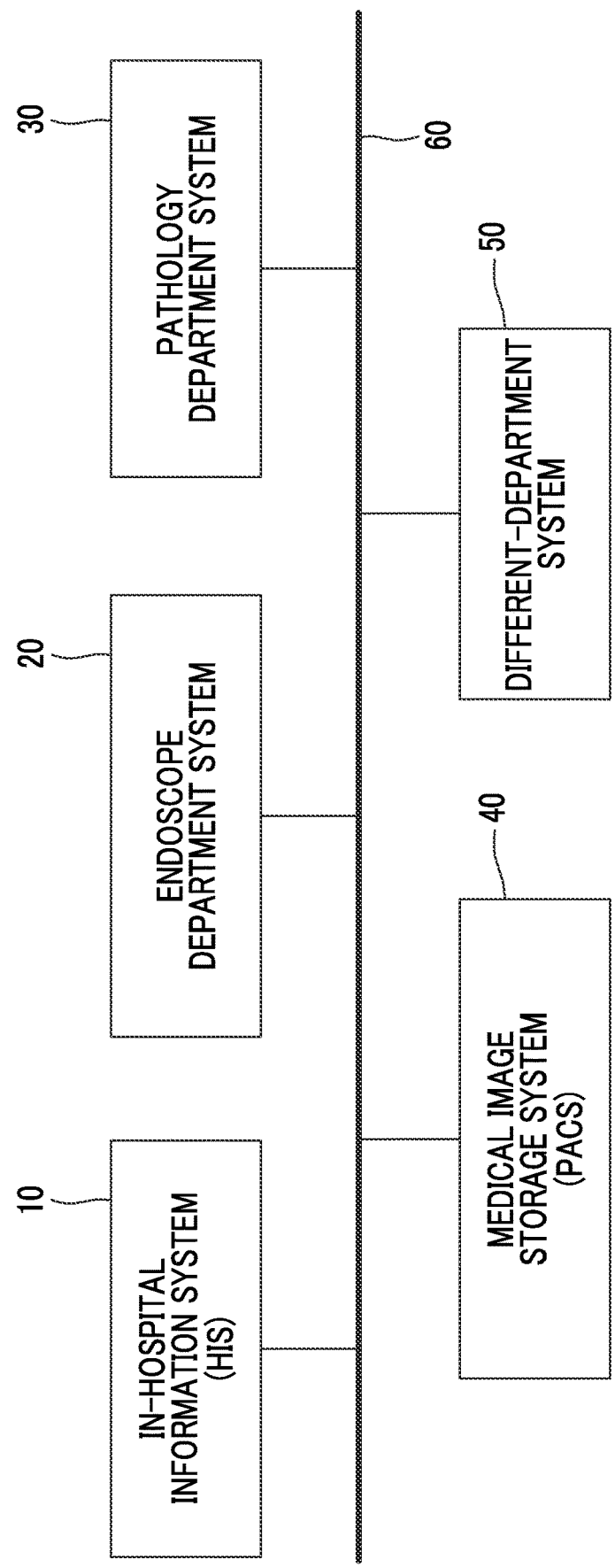
FIG. 1 is a diagram showing an example of an overall configuration of an in-hospital system.

FIG. 1 is a diagram showing an example of an overall configuration of an in-hospital system. The system shown in FIG. 1 comprises a hospital information system (HIS) 10, an endoscope department system 20, a pathology department system 30, a medical image storage system 40, and a different-department system 50. The HIS 10, the endoscope department system 20, the pathology department system 30, the medical image storage system 40, and the different-department system 50 are connected to an in-hospital local area network (LAN) 60 and can cooperate with each other.

The HIS 10 is a comprehensive system including a medical office accounting system, a medical care reservation system, a medical care information system, and the like, and includes an electronic medical record database and the like. The electronic medical record database stores an electronic medical record that records medical care information of a patient.

In a case in which information (hereinafter referred to as examination request information) related to an examination request (order) in a case in which the examination request is made to an endoscope department from other medical care departments is issued, the information is transmitted to the endoscope department system 20 via the HIS 10.

Examples of the examination request information include patient information, order key information ("order number", "date and time of occurrence", and the like), request source information ("request department name", "request doctor name", and the like), order information ("request disease name", "examination purpose", "examination type", "examination item", "examination site", "comment", and the like), and examination reservation information ("examination date", "performance time point", and the like). The patient information is information related to the patient and includes patient-peculiar information, such as "patient ID", "patient name", "date of birth", "age", "gender", and "inpatient/outpatient classification".

The endoscope department system 20 is a system that manages the endoscope department.

The pathology department system 30 is a system that manages a pathology department.

The medical image storage system 40 is a system that electronically stores, searches for, and analyzes an examination image from a medical image diagnosis device, such as an endoscope apparatus, a computed tomography (CT), and a magnetic resonance imaging (MRI). The medical image storage system 40 may be, for example, a picture archiving and communication systems (PACS) or may be another system capable of storing a medical image.

The different-department system 50 is a system that manages other departments.

Figure 2:
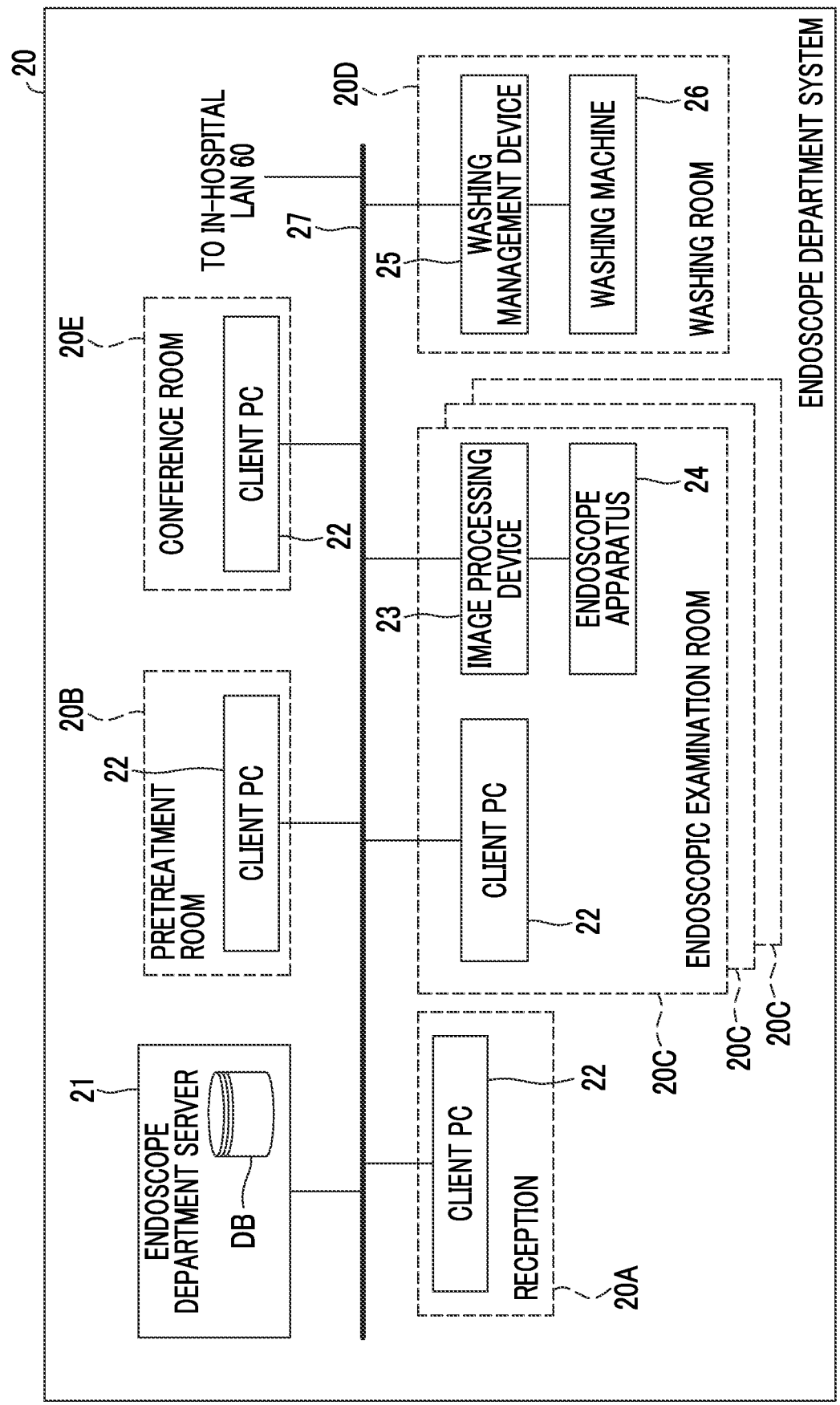
FIG. 2 is a diagram showing a schematic configuration of an endoscope department system in the system shown in FIG. 1.

FIG. 2 is a diagram showing a schematic configuration of the endoscope department system in the system shown in FIG. 1. The endoscope department includes a reception 20A, a pretreatment room 20B, a plurality of endoscopic examination rooms (hereinafter referred to as examination rooms) 20C, a washing room 20D, and a conference room 20E.

The reception 20A is a place at which the reception of the examination is made. The pretreatment room 20B is a room in which an interview and a pretreatment are performed before the endoscopic examination. The examination room 20C is a room in which the endoscopic examination is performed. The washing room 20D is a room in which a scope and the like used for the endoscopic examination is washed.

The endoscope department system 20 shown in FIG. 2 comprises an endoscope department server 21, a plurality of client personal computers (PCs) 22, an image processing device 23, an endoscope apparatus 24, a washing management device 25, and a washing machine 26. The endoscope department server 21, the plurality of client PCs 22, the image processing device 23, and the washing management device 25 are connected to an in-department LAN 27. The in-department LAN 27 is connected to the in-hospital LAN 60.

The image processing device 23 and the endoscope apparatus 24 are installed in each of a plurality of examination rooms 20C. The image processing device 23 and the endoscope apparatus 24 perform synchronization processing of synchronizing the internal time points thereof by communicating with each other.

The endoscope apparatus 24 comprises an insertion part (scope) having an imaging element at a distal end thereof, and inputs continuous captured image data obtained by continuous imaging of the imaging element to the image processing device 23. A configuration example of the endoscope apparatus 24 will be described below in FIG. 5.

In addition, the endoscope apparatus 24 generates a first still image based on the captured image data obtained by the imaging element when there is an acquisition operation of the still image (for example, pressing a button) from an operator of the endoscope apparatus 24. The first still image is a manually acquired image, which is acquired by the acquisition operation from the operator. In addition, the endoscope apparatus 24 adds information on an imaging time point, which is the internal time point of the endoscope apparatus 24 when the first still image is obtained, to the generated first still image. Moreover, the endoscope apparatus 24 inputs the generated first still image to the image processing device 23.

The image processing device 23 is connected to the endoscope apparatus 24 in the examination room 20C in which the image processing device 23 is installed. The image processing device 23 constitutes an analysis device that receives the captured image data from the endoscope apparatus 24.

The captured image data obtained by continuous imaging of the endoscope apparatus 24 are continuously input to the image processing device 23. The image processing device 23 generates a second still image based on the captured image data at a time different from the time when the acquisition operation of the still image is performed from the operator of the endoscope apparatus 24 among the captured image data continuously input from the endoscope apparatus 24. The second still image is an automatically acquired image, which is acquired without the acquisition operation from the operator. In addition, the image processing device 23 adds information on an imaging time point, which is the internal time point of the image processing device 23 when the second still image is obtained, to the generated second still image.

For example, the image processing device 23 performs analysis by artificial intelligence (AI) based on the captured image data which are continuously input. Moreover, the image processing device 23 generates a second still image based on the captured image data at a time based on a result of analysis among the captured image data continuously input from the endoscope apparatus 24. The time based on the result of the analysis is an example of the time different from the time when the acquisition operation described above is performed, for example, when a specific finding is detected based on the captured image data. The specific finding is, for example, a lesion, such as a malignant tumor, but is not limited to this, and can be various specific findings.

In addition, the image processing device 23 transmits the first still image input from the endoscope apparatus 24 and the generated second still image to the endoscope department server 21 via the in-department LAN 27. The first still image and the second still image transmitted by the image processing device 23 are stored by the medical image storage system 40 shown in FIG. 1, for example, under the control of the endoscope department server 21.

It should be noted that, although the configuration has been described in which the first still image generated by the endoscope apparatus 24 is transmitted to the endoscope department server 21 via the image processing device 23, a configuration may be adopted in which the first still image is transmitted by the endoscope apparatus 24 to the endoscope department server 21 without going through the image processing device 23. In addition, as the endoscope apparatus 24, an apparatus may be used in which the image processing device 23 is integrated.

The washing machine 26 and the washing management device 25 are installed in the washing room 20D. The washing machine 26 is a device that washes the scope and the like used for the endoscopic examination.

The washing management device 25 is connected to the washing machine 26, and is a computer that registers information, such as a washing history by the washing machine 26, in the endoscope department server 21.

The endoscope department server 21 is a computer that comprehensively controls the client PC 22, the image processing device 23, and the washing management device 25. The endoscope department server 21 has a built-in database DB, and various pieces of information (examination request information, examination result information, and the like) are stored in the database DB.

A predetermined application program is installed in the client PC 22, and the program enables reference and editing of data recorded in the database DB, registration of data in the database, and the like.

Figure 3:
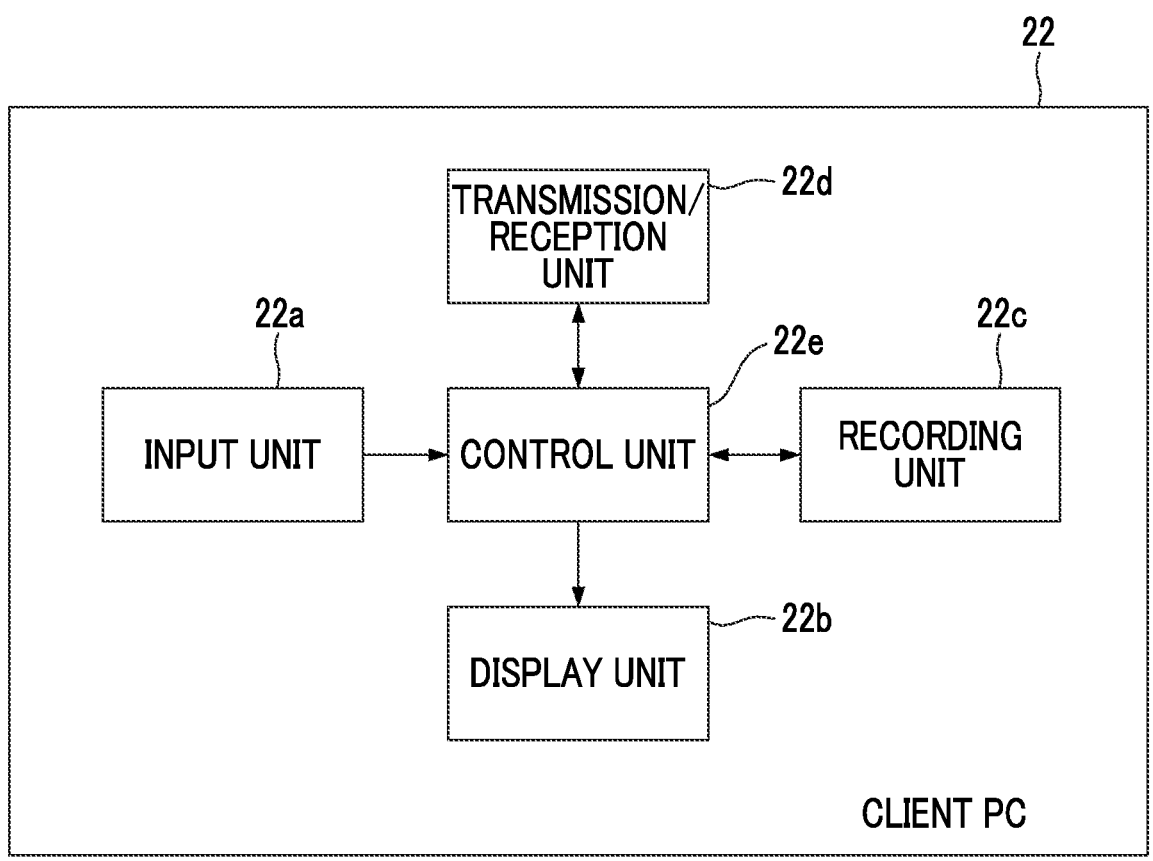
FIG. 3 is a block diagram showing an internal configuration of a client PC in an endoscope department system shown in FIG. 2.

FIG. 3 is a block diagram showing an internal configuration of the client PC in the endoscope department system shown in FIG. 2. As shown in FIG. 3, each client PC 22 is composed of an input unit 22a, the display unit 22b, a recording unit 22c, a transmission/reception unit 22d, and a control unit 22e.

The input unit 22a is an input unit that performs various inputs, and is composed of an input device, such as a keyboard and a touch panel, and a pointing device, such as a mouse and a trackball.

The display unit 22b is a display that displays various images, reports, and the like, and is composed of a liquid crystal display (LCD), a cathode ray tube (CRT), and the like.

The recording unit 22c is composed of a hard disk or the like that records various data.

The transmission/reception unit 22d is composed of a transmission/reception interface circuit and the like, and executes processing of transmitting/receiving various instructions, various requests, and various data via the in-department LAN 27.

The control unit 22e includes various processors that execute a program to perform processing, a random access memory (RAM), and a read only memory (ROM).

Examples of the various processors include a central processing unit (CPU), which is a general-purpose processor that executes the program to perform various pieces of processing, a programmable logic device (PLD), which is a processor of which the circuit configuration can be changed after the manufacture, such as a field programmable gate array (FPGA), and a dedicated electric circuit, which is a processor having the circuit configuration specially designed for executing specific processing, such as an application specific integrated circuit (ASIC).

More specifically, the structure of these various processors is an electric circuit in which circuit elements, such as semiconductor elements, are combined.

The control unit 22e may be composed of one of the various processors, or may be composed of a combination (for example, a combination of a plurality of FPGAs or a combination of a CPU and an FPGA) of two or more processors of the same type or different types.

The control unit 22e controls each unit of the client PC 22 in accordance with the program described above, various requests transmitted from an outside via the in-department LAN 27, instruction information input from the input unit 22a, and the like.

FIG. 4 is a diagram showing an example of a basic screen of an application of the client PC 22. In a case in which the user activates the application on the client PC 22 and logs in, the control unit 22e acquires basic screen data from the database DB and displays the basic screen shown in FIG. 4 on the display unit 22b. It should be noted that the client PC 22 is, for example, the client PC 22 in the examination room 20C, but the client PC 22 is not limited to this, and may be another client PC 22 shown in FIG. 2.

This basic screen is composed of a region A in which a list of the examination request information (partially excerpted information) is displayed, a region B in which various operation buttons are displayed, and a region C in which a valid launcher for the examination request information selected from the list of the region A is displayed.

In the list of the region A, processing items, such as "visit", "reception", "examination", and "counting" are provided for each examination request information, and an "o" mark is displayed for each processing item in a case in which the processing indicated by each processing item for the each examination request information ends.

The data for displaying the mark is registered in the database DB by the endoscope department server 21 in a case in which each processing ends. For example, in a case in which the examination based on the examination request information ends, the endoscope department server 21 registers the information indicating that the examination ends in the database DB in association with the examination request information. As a result, the "o" mark is displayed in the processing item of "examination". The information on whether or not each processing ends may be manually input, or it may be possible to automatically give a notification thereof from the client PC 22 or the endoscope apparatus 24.

The application has a button C1 of "report" as the operation button, and the button C1 of "report" is displayed in the region C of the basic screen shown in FIG. 4. This button C1 is a button for performing creation work of a report for the examination based on the examination request information selected from the list of the region A.

The control unit 22e of the client PC 22 periodically acquires the data for displaying the basic screen from the database DB and displays the basic screen on the display unit 22b.

In the system shown in FIG. 2, the control unit 22e of the client PC 22 supports the selection of the still image to be inserted in the report by a report creator (for example, a doctor) in a case in which an instruction to create the report for the performed examination is given.

Figure 5:
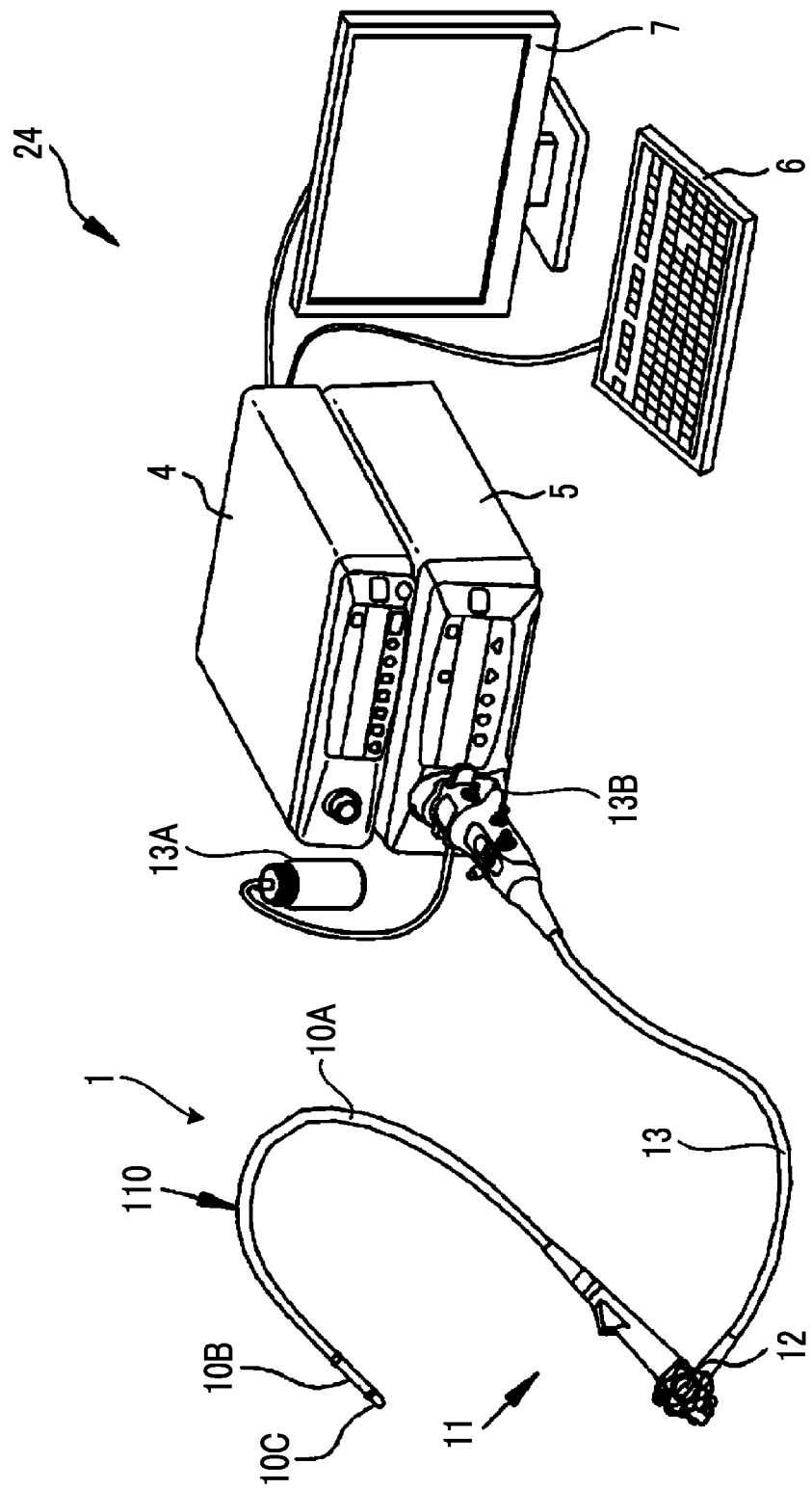
FIG. 5 is a diagram showing an example of an endoscope apparatus 24.

FIG. 5 is a diagram showing an example of the endoscope apparatus 24. As shown in FIG. 5, the endoscope apparatus 24 comprises an endoscope 1, and a control device 4 and a light source device 5 to which the endoscope 1 is connected.

A display device 7 that displays a captured image or the like obtained by imaging an inside of a subject by the endoscope 1 and an input unit 6, which is an interface for inputting various pieces of information to the control device 4 are connected to the control device 4. The control device 4 controls the endoscope 1, the light source device 5, and the display device 7.

The display device 7 has a display surface on which display pixels are two-dimensionally arranged, and pixel data constituting image data is drawn on each display pixel on the display surface, thereby performing the display of an image based on the image data. The display device 7 constitutes a display unit that switches the display image in response to a command from the control device 4.

The endoscope 1 includes an insertion part 110 which is a tubular member extending in one direction and is inserted into the subject, an operating part 11 which is provided in a base end part of the insertion part 110 and includes an operation member for performing an observation mode switching operation, an imaging recording operation, a forcep operation, an air supply/water supply operation, and a suction operation, an angle knob 12 provided adjacent to the operating part 11, and a universal cord 13 including connector portions 13A and 13B that detachably connect the endoscope 1 to the control device 4 and the light source device 5, respectively.

It should be noted that, although not shown in FIG. 5, various channels, such as a forcep hole for inserting forceps for sampling a living body tissue, such as cells or polyps, an air supply/water supply channel, and a suction channel, are provided inside the operating part 11 and the insertion part 110.

The insertion part 110 is composed of a flexible part 10A having flexibility, a bendable part 10B provided at a distal end of the flexible part 10A, and a hard distal end part 10C provided at a distal end of the bendable part 10B.

The bendable part 10B is configured to be bendable by a rotational movement operation of the angle knob 12. Depending on a site of the subject in which the endoscope 1 is used, the bendable part 10B can be bent in any direction and at any angle, and the distal end part 10C can be directed in a desired direction.

Figure 6:
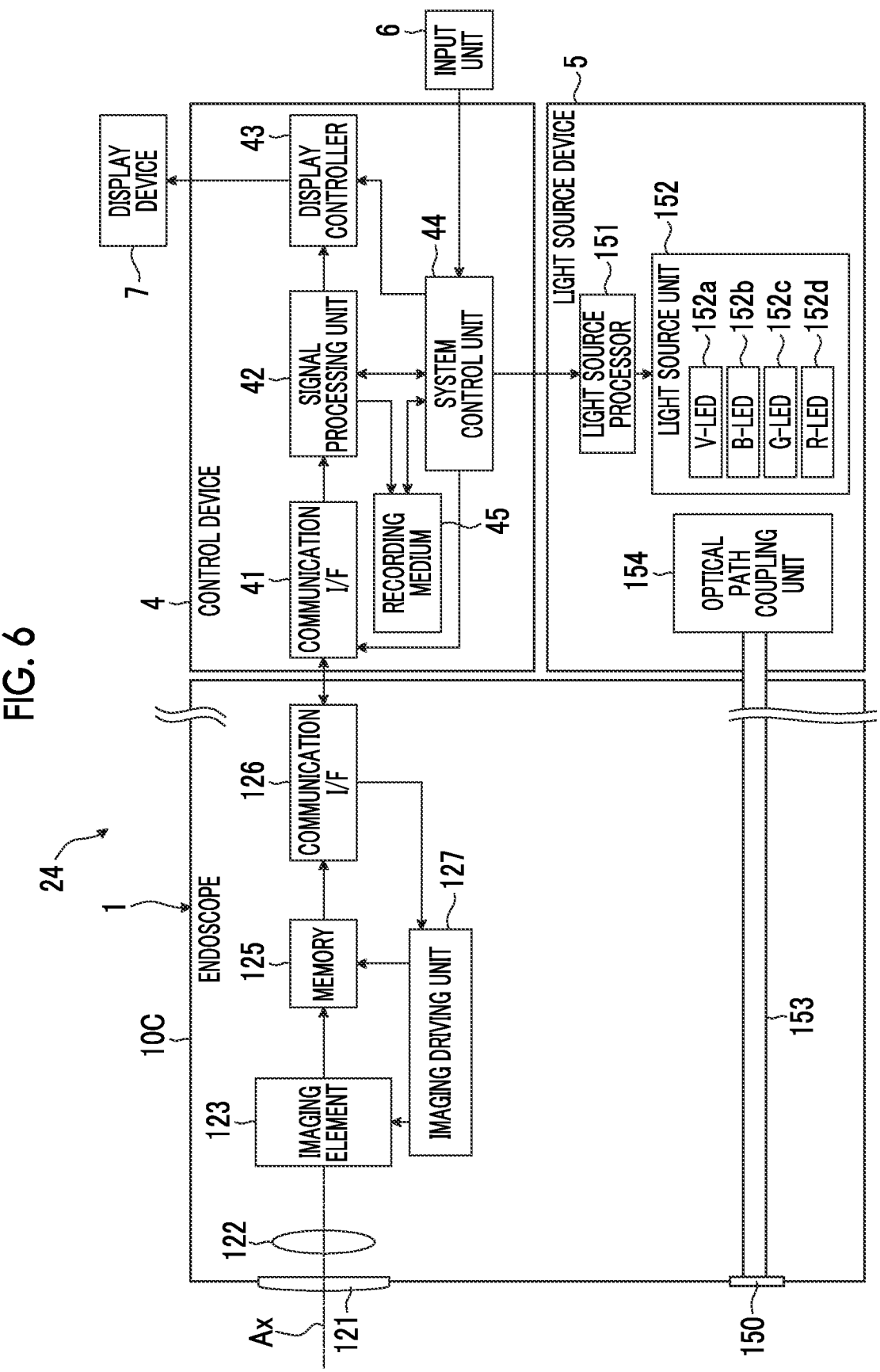
FIG. 6 is a schematic view showing an internal configuration of the endoscope apparatus 24 shown in FIG. 5.
Figure 7:
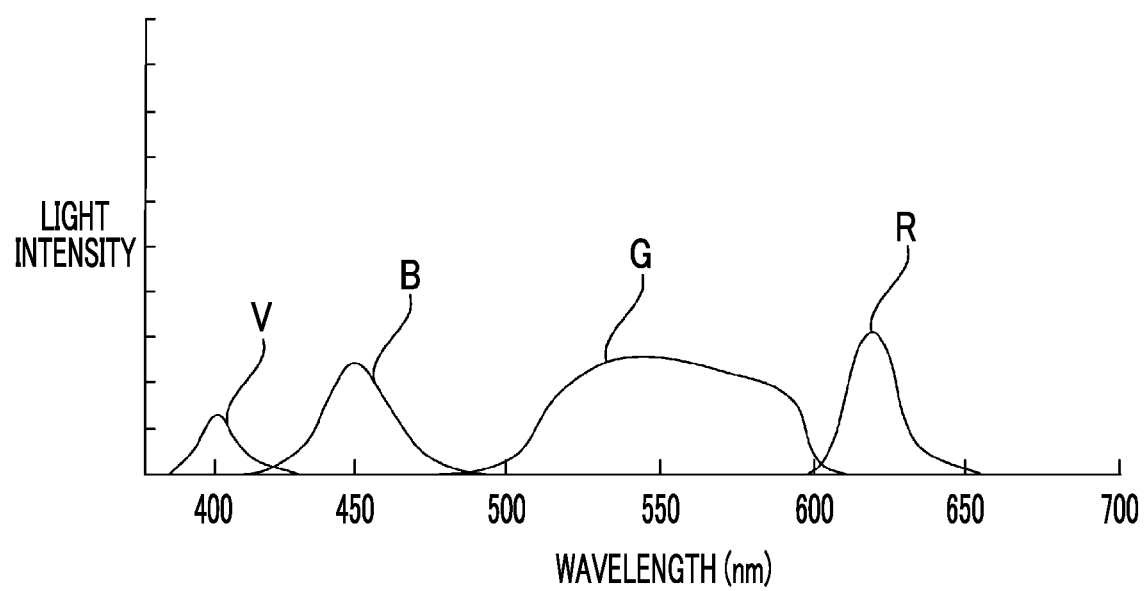
FIG. 7 is a diagram showing an example of a spectrum of light generated by a light source device 5 shown in FIG. 6.

FIG. 6 is a schematic view showing an internal configuration of the endoscope apparatus 24 shown in FIG. 5. FIG. 7 is a diagram showing an example of a spectrum of light generated by the light source device 5 shown in FIG. 6.

The light source device 5 can perform irradiation while switching normal light and special light as illumination light. The normal light is light having an emission spectrum suitable for recognition by a human, such as a doctor, such as white light. The special light is light having an emission spectrum suitable for analysis by a computer, such as image-enhanced endoscopy (IEE), which has a different emission spectrum from the normal light.

Specifically, the light source device 5 comprises a light source processor 151, a light source unit 152, and an optical path coupling unit 154. The light source processor 151 is connected to the system control unit 44 of the control device 4, and controls the light source unit 152 based on the command from a system control unit 44.

The light source unit 152 has, for example, a plurality of semiconductor light sources, each of which is turned on or off, and in a case in which the light source unit 152 is turned on, the emission amount of each semiconductor light source is controlled to emit the illumination light for illuminating an observation target. In the present embodiment, the light source unit 152 has LEDs of four colors, a violet light emitting diode (V-LED) 152a, a blue light emitting diode (B-LED) 152b, a green light emitting diode (G-LED) 152c, and a red light emitting diode (R-LED) 152d.

By independently controlling each of the V-LED 152a, the B-LED 152b, the G-LED 152c, and the R-LED 152d, the light source processor 151 can emit violet light V, blue light B, green light G, or red light R by independently changing a light amount. As shown in FIG. 7, the V-LED 152a generates the violet light V of which a central wavelength is in a range of 405±10 nm and a wavelength range is in a range of 380 to 420 nm. The B-LED 152b generates the blue light B of which a central wavelength is in a range of 450±10 nm and a wavelength range is in a range of 420 to 500 nm. The G-LED 152c generates the green light G of which a wavelength range is in a range of 480 to 600 nm. The R-LED 152d generates the red light R of which a central wavelength is in a range of 620 to 630 nm and a wavelength range is in a range of 600 to 650 nm.

In addition, in a case of irradiation with the normal light, the light source processor 151 controls each of the LEDs 152a to 152d to emit the white light in which a light amount ratio of the violet light V, the blue light B, the green light G, and the red light R is Vc:Bc:Gc:Rc. It should be noted that Vc, Bc, Gc, Rc>0.

In addition, in a case of irradiation with the special light, the light source processor 151 controls each of the LEDs 152a to 152d to emit the special light in which the light amount ratio of the violet light V, the blue light B, the green light G, and the red light R as short-wavelength narrow band light is Vs:Bs:Gs:Rs.

The light amount ratio Vs:Bs:Gs:Rs is different from the light amount ratio Vc:Bc:Gc:Rc used in a case of the irradiation with the normal light, and is appropriately determined in accordance with the observation purpose. For example, in a case in which superficial blood vessels are enhanced, it is preferable to make Vs larger than Bs, Gs, and Rs, and in a case in which mesopelagic blood vessels are enhanced, it is preferable to make Gs larger than Vs, Gs, and Rs.

The optical path coupling unit 154 combines each light emitted from the V-LED 152a, the B-LED 152b, the G-LED 152c, and the R-LED 152d, and emits the combined light as the illumination light. The illumination light emitted from the optical path coupling unit 154 of the light source unit 152 enters a light guide 153, which will be described below, built in the universal cord 13, and is emitted to the subject through an illumination lens 150 provided at the distal end part 10C of the insertion part 110.

In the distal end part 10C of the endoscope 1, an imaging optical system including an objective lens 121 and a lens group 122, an imaging element 123 that images the subject through the imaging optical system, a memory 125, such as the RAM, a communication interface (I/F) 126, an imaging driving unit 127, and the light guide 153 for guiding the illumination light emitted from the light source unit 152 to the illumination lens 150 are provided. The imaging element 123 constitutes an imaging unit according to the embodiment of the present invention.

The light guide 153 extends from the distal end part 10C to the connector portion 13A of the universal cord 13. The illumination light emitted from the light source unit 152 of the light source device 5 is in a state of being capable of entering the light guide 153 in a state in which the connector portion 13A of the universal cord 13 is connected to the light source device 5.

A charge coupled device (CCD) image sensor or a complementary metal oxide semiconductor (CMOS) image sensor is used as the imaging element 123. In the present embodiment, the imaging element 123 is the CMOS using a rolling shutter.

The imaging element 123 has a light-receiving surface on which a plurality of pixels are two-dimensionally arranged, and converts an optical image formed on the light-receiving surface by the imaging optical system described above into an electrical signal (imaging signal) in each pixel. Moreover, the imaging element 123 converts the converted imaging signal from an analog signal into a digital signal having a predetermined number of bits, and outputs the imaging signal converted into the digital signal to the memory 125. For example, an imaging element on which a color filter, such as an elementary color or a complementary color, is mounted, is used as the imaging element 123.

The imaging element 123 may be disposed at the distal end part 10C in a state in which the light-receiving surface is perpendicular to an optical axis Ax of the objective lens 121, or may be disposed at the distal end part 10C in a state in which the light-receiving surface is parallel to the optical axis Ax of the objective lens 121.

The imaging optical system provided in the endoscope 1 is composed of optical members (including the lens group 122 described above), such as a lens and a prism, which are present on an optical path of the light from the subject between the imaging element 123 and the objective lens 121, and the objective lens 121. There is also a case in which the imaging optical system is composed of only the objective lens 121.

The memory 125 transitorily records the digital imaging signal output from the imaging element 123.

The communication I/F 126 is connected to a communication interface (I/F) 41 of the control device 4. The communication I/F 126 transmits the imaging signal recorded in the memory 125 to the control device 4 through a signal line in the universal cord 13.

The imaging driving unit 127 is connected to the system control unit 44 of the control device 4 via the communication I/F 126. The imaging driving unit 127 drives the imaging element 123 and the memory 125 based on the command from the system control unit 44 received by the communication I/F 126.

The control device 4 comprises the communication I/F 41, which is connected to the communication I/F 126 of the endoscope 1 by the universal cord 13, a signal processing unit 42, a display controller 43, the system control unit 44, and a recording medium 45.

The communication I/F 41 receives the imaging signal transmitted from the communication I/F 126 of the endoscope 1 to transmit the imaging signal to the signal processing unit 42.

The signal processing unit 42 has a memory that transitorily records the imaging signal received from the communication I/F 41 built therein, and performs processing (image processing, such as demosaicing processing or gamma-correction processing) on the captured image signal that is a set of the imaging signals recorded in the memory to generate captured image information in such a format that recognition processing to be described below or the like can be performed. The captured image information generated by the signal processing unit 42 is recorded on the recording medium 45, such as a hard disk or a flash memory.

The display controller 43 displays a captured image based on the captured image information generated by the signal processing unit 42 on the display device 7. A coordinate of each pixel data constituting the captured image information generated by the signal processing unit 42 is managed in association with a coordinate of any of the display pixels constituting the display surface of the display device 7.

The system control unit 44 controls each unit of the control device 4, and transmits the command to the imaging driving unit 127 of the endoscope 1 and the light source processor 151 of the light source device 5, and comprehensively controls the entire endoscope apparatus 24. For example, the system control unit 44 performs the control of the imaging element 123 via the imaging driving unit 127. In addition, the system control unit 44 performs the control of the light source unit 152 via the light source processor 151.

The system control unit 44 or the signal processing unit 42 includes the various processors that execute a program to perform processing, a RAM, and a ROM.

Examples of various processors include a CPU, which is a general-purpose processor that executes the program to perform various pieces of processing, a programmable logic device, which is a processor of which the circuit configuration can be changed after the manufacture, such as an FPGA, and a dedicated electric circuit, which is a processor having the circuit configuration specially designed for executing specific processing, such as an ASIC.

More specifically, the structure of these various processors is an electric circuit in which circuit elements, such as semiconductor elements, are combined.

The system control unit 44 or the signal processing unit 42 may be composed of one of the various processors, or may be composed of a combination (for example, a combination of a plurality of FPGAs or a combination of a CPU and an FPGA) of two or more processors of the same type or different types.

Next, specific examples of a method of switching the emission spectrum of the illumination light in the endoscope apparatus 24 and a method of generating the second still image in the image processing device 23 accompanying the switching of the emission spectrum of the illumination light in the endoscope apparatus 24 will be described.

For example, the endoscope apparatus 24 periodically switches the emission spectrum of the illumination light during continuous imaging by the endoscope apparatus 24. As an example, the endoscope apparatus 24 periodically performs switching of setting the illumination light to the normal light, such as the white light, for a time of 9 frames and setting the illumination light to the special light, such as narrow band light, for a time of one frame immediately after the normal light. The frame referred herein is a imaging frame by the endoscope apparatus 24. It should be noted that a ratio of the time of the normal light to the time of the special light in each period is not limited to 1:9 and can be set optionally.

In this case, the captured image data obtained by continuous imaging by the endoscope apparatus 24 includes captured image data obtained by imaging with the normal light (captured image data of the normal light) and captured image data obtained by imaging with the special light (captured image data of the special light).

The endoscope apparatus 24 displays, for example, an image of the normal light based on the captured image data of the normal light and an image of the special light based on the captured image data of the special light by the display device 7. Alternatively, the endoscope apparatus 24 may use the image of the special light based on the captured image data of the special light as a target of processing, such as the analysis, without displaying the image of the special light on the display device 7 (that is, in the background).

In addition, the endoscope apparatus 24 inputs at least one of the captured image data of the normal light or the captured image data of the special light among the captured image data obtained by continuous imaging to the image processing device 23.

The image processing device 23 may detect the specific finding based on the captured image data of the normal light among the captured image data continuously input from the endoscope apparatus 24, may detect the specific finding based on the captured image data of the special light, and may detect the specific finding based on both the captured image data.

In addition, in a case in which the specific finding is detected based on, for example, the captured image data of the normal light, the image processing device 23 generates the second still image of the normal light based on the captured image data. Alternatively, in a case in which the specific finding is detected based on the captured image data of the special light, the image processing device 23 generates the second still image of the special light based on the captured image data.

Alternatively, in a case in which the specific finding is detected based on the captured image data of the special light, the image processing device 23 may generate both the second still image of the special light based on the captured image data of the special light and the second still image of the normal light based on the captured image data of the normal light. In this case, the captured image data of the normal light is, for example, the captured image data having the imaging time point closest to the imaging time point of the captured image data of the special light in which the specific finding is detected, among the captured image data of the normal light input from the endoscope apparatus 24 to the image processing device 23.

Although the case has been described in which the endoscope apparatus 24 alternately switches the illumination light between the normal light and the special light, the switching of the illumination light is not limited to this. That is, the endoscope apparatus 24 may periodically switch the illumination light between two or more illumination light beams having different emission spectra. For example, the endoscope apparatus 24 may periodically perform switching between the normal light, first special light, and second special light having a different emission spectrum from the first special light. The image processing device 23 detects the specific finding based on the captured image data of any emission spectrum among the captured image data continuously input from the endoscope apparatus 24.

Figure 8:
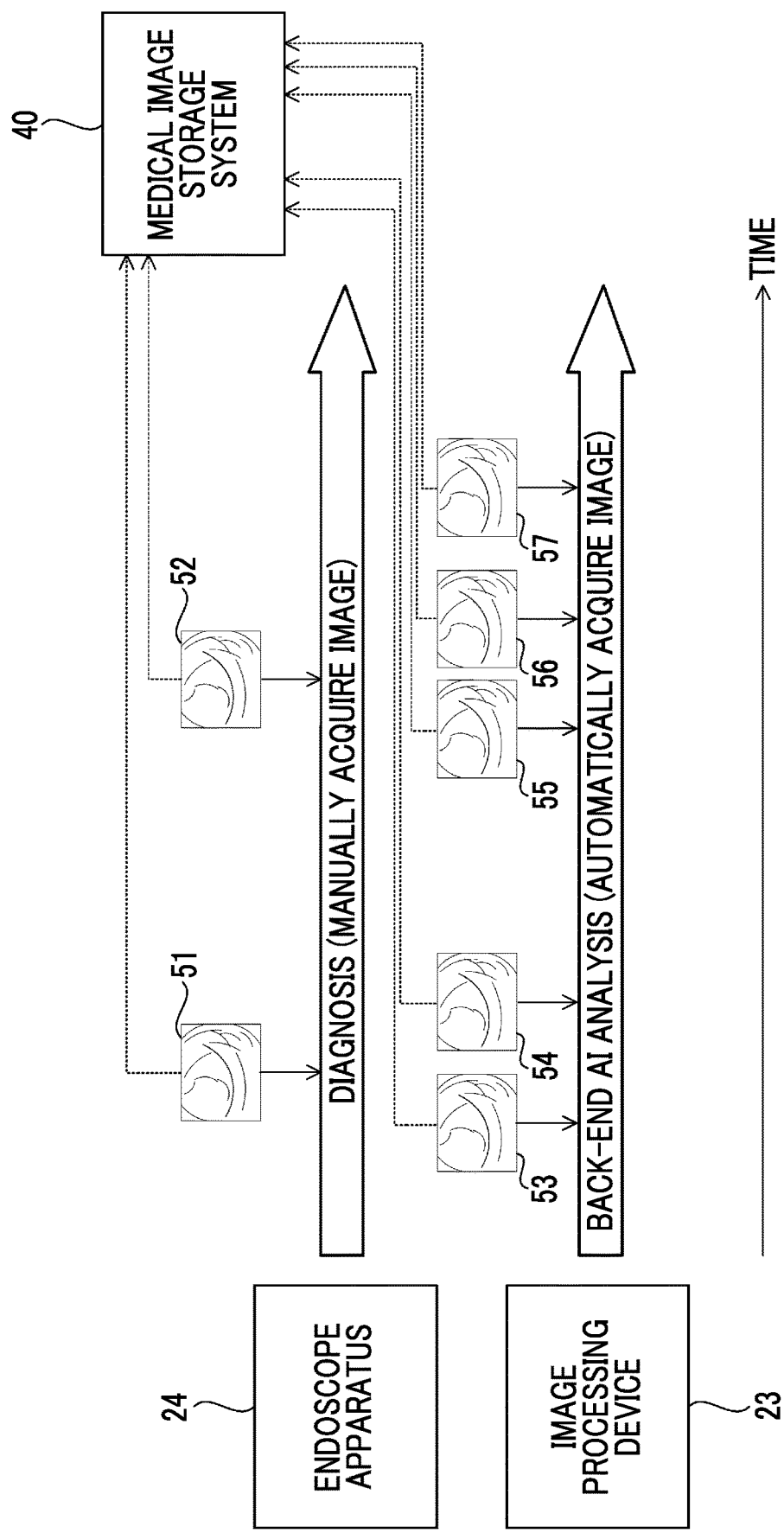
FIG. 8 is a diagram showing an example of the accumulation of a first still image and a second still image.

FIG. 8 is a diagram showing an example of the accumulation of the first still image and the second still image. In FIG. 8, a horizontal axis represents a time.

For example, during the diagnosis using the endoscope apparatus 24, the doctor performs the acquisition operation of the still image with respect to the endoscope apparatus 24 while seeing a live image displayed on a display (for example, a display device 7 shown in FIG. 5) of the endoscope apparatus 24 at any timing, such as a case in which the specific finding is detected.

As a result, the first still image is generated in the endoscope apparatus 24. In the example shown in FIG. 8, manually acquired images 51 and 52 are generated as the first still image. The manually acquired images 51 and 52 are accumulated in the medical image storage system 40 together with time point information indicating a time point when the manually acquired images 51 and 52 are generated, respectively.

In addition, in parallel with the examination by the doctor, the image processing device 23 detects the specific finding (for example, the lesion, such as the malignant tumor) by the analysis by the AI based on the captured image data continuously input from the endoscope apparatus 24. The analysis by the AI is, for example, a back-end AI analysis performed in a state invisible to the doctor or the like (at the back-end).

For example, the image processing device 23 calculates an index value of mucous membrane information by the AI from the captured image data obtained by imaging the observation target by the endoscope apparatus 24. The index value is, for example, a value indicating a state of at least one of blood vessel, duct, redness, fold, or mucus of the observation target represented by the image signal. Moreover, the image processing device 23 detects the lesion (specific finding), such as the malignant tumor, by determining whether or not the mucous membrane information (mucous membrane state), which is the observation target, corresponds to the lesion, such as the malignant tumor, based on the calculated index value.

The image processing device 23 generates the second still image based on the captured image data when the specific finding is detected by the back-end AI analysis among the captured image data continuously input from the endoscope apparatus 24. In the example shown in FIG. 8, automatically acquired images 53 to 57 are generated as the second still image. The automatically acquired images 53 to 57 are accumulated in the medical image storage system 40 together with time point information indicating a time point when the automatically acquired images 53 to 57 are generated, respectively.

Figure 9:
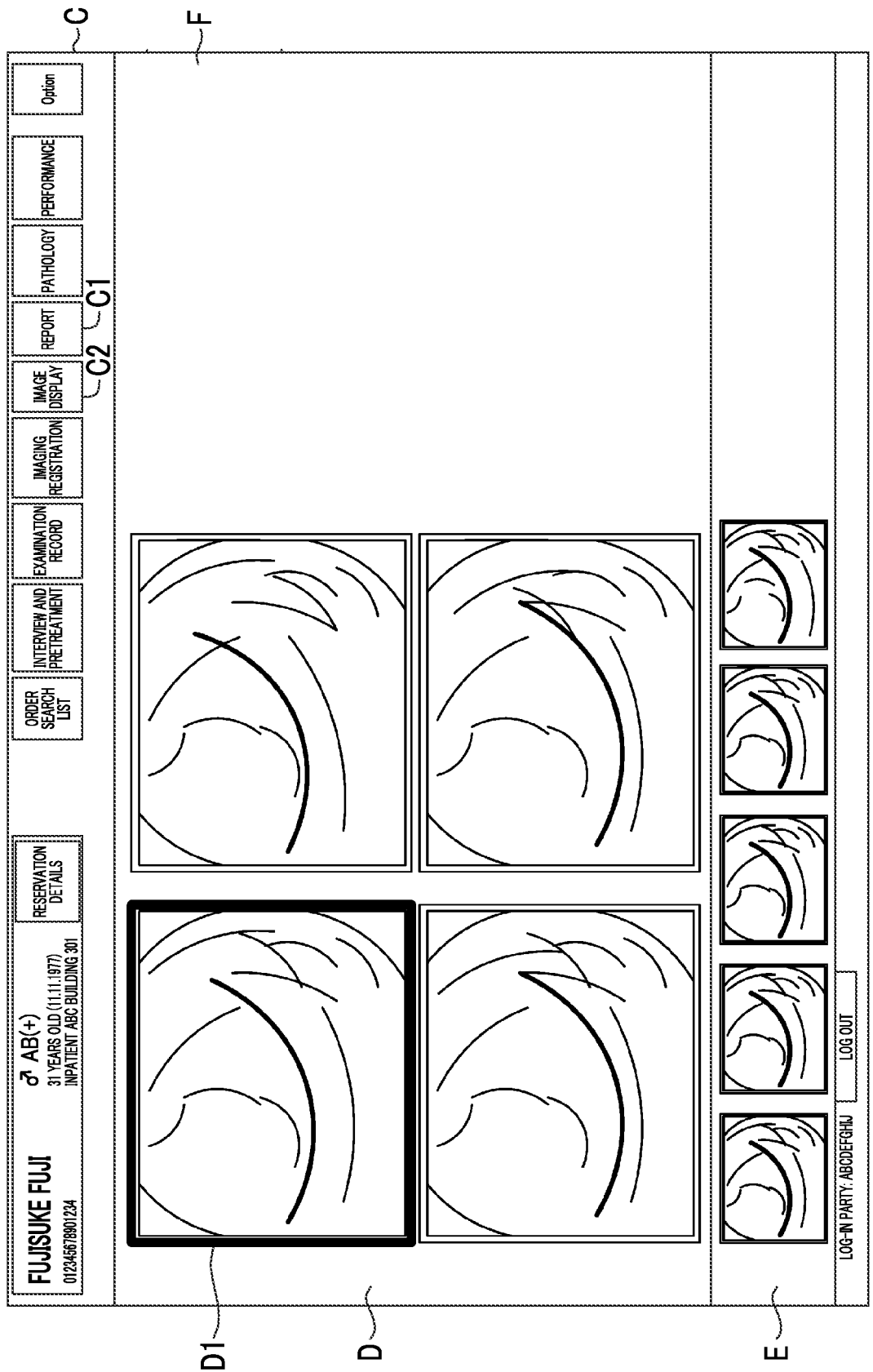
FIG. 9 is a diagram showing an example of an image selection screen of the client PC 22.

FIG. 9 is a diagram showing an example of an image selection screen of the client PC 22. After the first still image and the second still image are accumulated in the medical image storage system 40 by the diagnosis using the endoscope apparatus 24, in a case in which an instruction of a button "screen display" included in the region C2 of the basic screen is performed, regions D to F are displayed instead of the regions A and B shown in FIG. 2.

In the region F, an operating part, such as a button for performing various operations on the regions D and E, is disposed.

In the regions D and E, the first still image (manually acquired image) and the second still image (automatically acquired image) generated for a target patient are generated. The control unit 22*e* of the client PC 22 displays these still images by acquiring the still images from the medical image storage system 40.

In the region D, the first still images generated for the target patient are displayed side by side. In the example shown in FIG. 9, four first still images are displayed in the region D. It should be noted that more first still images may be able to be displayed in the region D by scrolling the screen or the like.

A thick frame D1 is displayed to surround the selected first still image among the first still images displayed in the region D. In the example shown in FIG. 9, the first still image on an upper left is selected. For example, by operating the operating part of the region F, the selected first still image among the first still images displayed in the region D is switched, and the thick frame D1 is also moved accordingly.

In the region E, the automatically acquired images having the imaging time point that satisfies a predetermined condition with the imaging time point of the first still image selected in the region D among the second still images generated for the target patient are displayed side by side as a third still image.

Specifically, the control unit 22*e* extracts the second still images having the time point information of which a difference from the time point information of the selected first still image is equal to or less than a threshold value (prescribed value) from among the second still images, and displays the extracted second still images side by side in the region E as the third still image. The threshold value is, for example, a value in a range of several seconds to several tens of seconds, but is not limited to the value in this range. In the example shown in FIG. 9, five second still images are displayed in the region E as the third still image.

As described above, the control unit 22*e* displays the first still image and the third still image in association with each other on the display unit 22*b*. Displaying the first still image and the third still image in association with each other means displaying the first still image and the third still image in a comparable manner, for example, as shown in FIG. 9, simultaneously displaying the first still image and the third still image in different regions of the display unit 22*b*.

The report creator can select a key image from among the first still image and the third still image displayed in association with each other by operating the operating part in the region F. The key image is one or more still images that are inserted into the report. In the example shown in FIG. 9, the report creator can select the key image from one first still image in the upper left of the region D and five third still images in the region E. The selected key image constitutes a selected still image for which the selection operation by the user is performed from the first still image and the third still image, and is a candidate image for an image to be inserted into the examination report by the endoscope apparatus 24.

The first still image and the third still image are still images of which the imaging time points are close to each other. As a result, the report creator can select any of the manually acquired first still image or the third still image automatically acquired simultaneously with the first still image as the key image. Therefore, for example, in a case in which a quality of the first still image is poor (for example, the blur is large), an image having a good quality can be selected and replaced from among the third still images.

In addition, in a case in which the report creator switches the selected first still image in the region D to the first still image on the upper right by operating the operating part in the region F, the control unit 22*e* extracts the second still images having the time point information of which a difference from the time point information of the first still image on the upper right is equal to or less than the threshold value from among the second still images, and displays the extracted second still images side by side in the region E as the third still image. In this case as well, the report creator can select a key image from among the first still image and the third still image displayed in association with each other.

The report creator also selects the key image from the first still image and the third still image for the other first still images in the region D. It should be noted that, it may be possible to delete a part of the first still image in the region D by operating the operating part in the region F.

Figure 10:
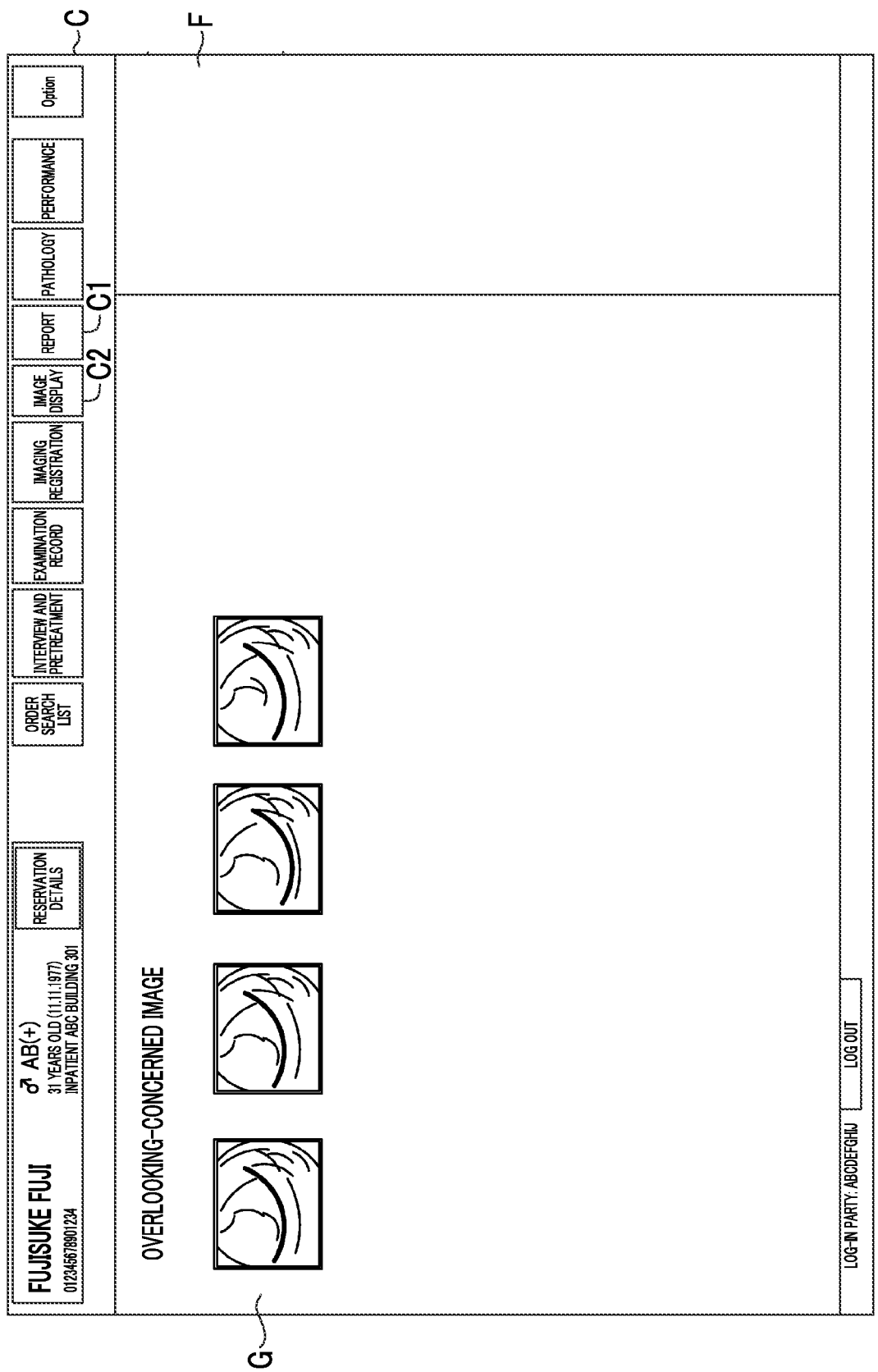
FIG. 10 is a diagram showing an example of an overlooking-concerned image display screen of the client PC 22.

FIG. 10 is a diagram showing an example of an overlooking-concerned image display screen of the client PC 22. By operating the operating part of the region F shown in FIG. 9, the control unit 22*e* displays the region G on the display unit 22*b* instead of the regions D and E.

In the region G, the fourth still images extracted by the control unit 22*e* from the second still images are displayed side by side. The fourth still image is the second still image having the imaging time point that does not satisfy the condition described above with the imaging time points of all the first still images in the region D among the second still images.

Specifically, in a case in which the region G is displayed instead of the regions D and E, the control unit 22*e* extracts the second still images having the time point information of which the difference with the time point information of all the first still images in the region D is more than the threshold value from among the second still images, and displays the extracted second still images side by side on the region G as a fourth still image.

That is, the fourth still image is the second still image obtained by automatic imaging based on the back-end AI analysis in a time slot when the acquisition operation of the still image is not performed. Therefore, the fourth still image includes an image that is concerned to be overlooked during the examination by the endoscope apparatus 24.

The report creator can select the key image from among the fourth still images displayed in the region G by operating the operating part in the region F.

As a result, even in a case in which the operator of the endoscope apparatus 24 (for example, the doctor) forgets the acquisition operation of the still image or fails the acquisition operation, the key image can be selected from among the automatically acquired fourth still images and interpolated. In addition, the operator of the endoscope apparatus 24 can focus only on a clear lesion or the like found by himself/herself and perform the acquisition operation of the still image.

In the example shown in FIG. 10, the case has been described in which only the extracted fourth still image is displayed in the region G, but a display method of the fourth still image is not limited to this. For example, the control unit 22e may display a plurality of fourth still images side by side in time series together with the time point information. Alternatively, the control unit 22e may display the fourth still image together with the selected key image on the screen shown in FIG. 9 in time series. As a result, the report creator can easily grasp at which stage the fourth still image, which is concerned to be overlooked, is during the examination by the endoscope apparatus 24.

After the key image on the screens shown in FIGS. 9 and 10 is selected, in a case in which the report creator performs the instruction of the button C1 of "report" in the region C, a report creation screen for performing the creation work of the report is displayed on the display unit 22b.

Moreover, on the report creation screen, each still image selected as the key image by each operation described in FIG. 9 can be selected as the image to be inserted into the report. As a result, the report operator can easily create the report into which an appropriate key image selected from the first still image (manually acquired image) and the second still image (automatically acquired image) is inserted.

The created report is stored in, for example, the database DB of the endoscope department server 21.

Figure 11:
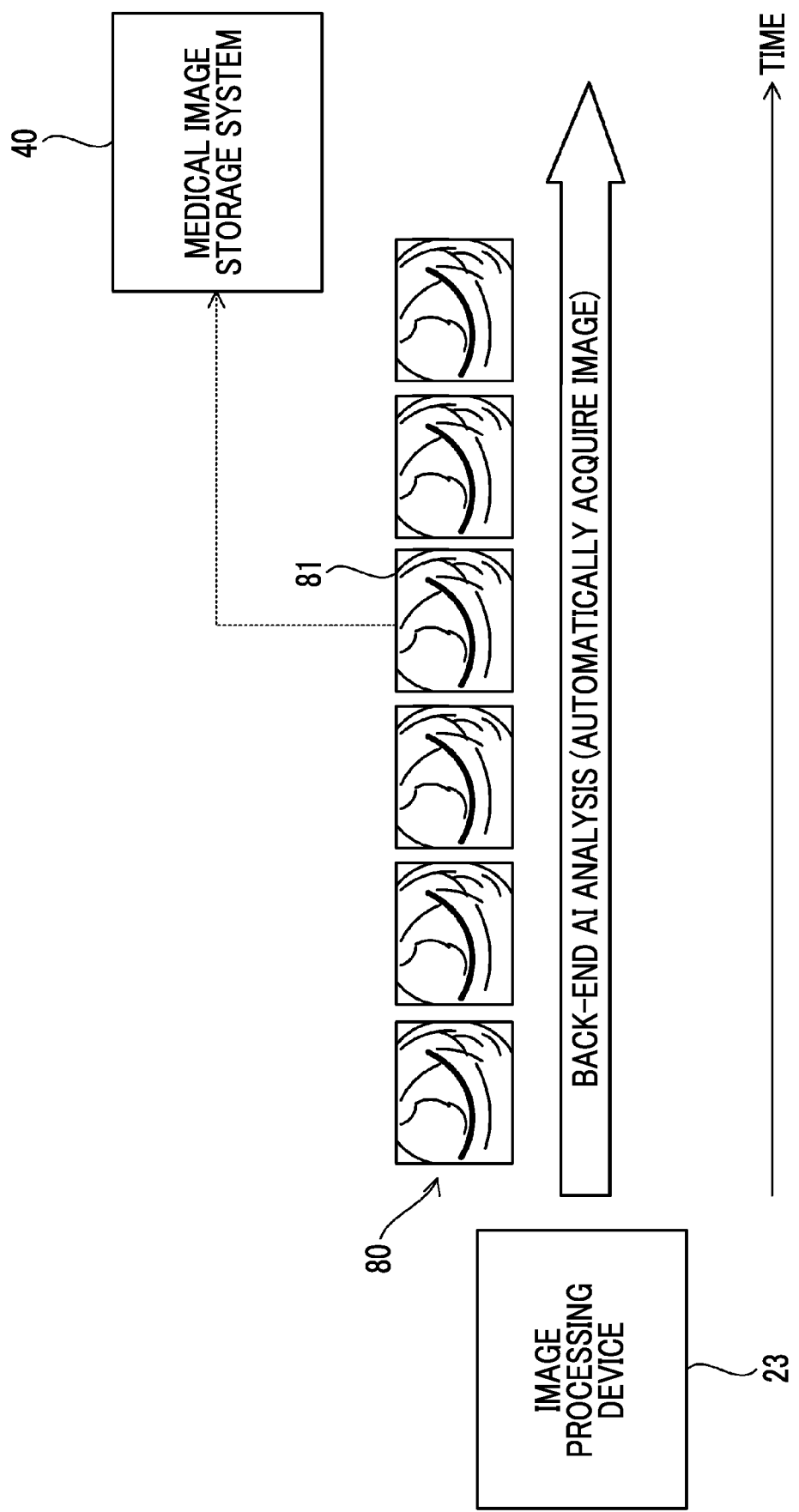
FIG. 11 is a diagram showing an example of a back-end AI analysis by an image processing device 23.

FIG. 11 is a diagram showing an example of a back-end AI analysis by the image processing device 23. In FIG. 11, a horizontal axis represents a time. A captured image data group 80 is the captured image data continuously input from the endoscope apparatus 24 to the image processing device 23.

As an example of the back-end AI analysis, the image processing device 23 calculates a correct diagnosis rate based on the captured image data of each of the captured image data included in the captured image data group 80. The correct diagnosis rate is a probability that a correct diagnosis is made by the still image based on the captured image data. The calculation of the correct diagnosis rate based on the captured image data can be performed using, for example, an AI model trained by a large number of samples of a combination of the captured image data and the correct diagnosis rate.

Moreover, in a case in which the captured image data in which the calculated correct diagnosis rate is equal to or more than a threshold value (for example, 90%) is continuous by a certain number (for example, six frames), the image processing device 23 generates the second still image based on at least a part of the continuous captured image data. In the example shown in FIG. 11, the image processing device 23 generates the second still image based on the captured image data 81 in the captured image data group 80. Moreover, the image processing device 23 accumulates the generated second still image in the medical image storage system 40 via the endoscope department server 21.

FIG. 12 is a sequence diagram showing an example of normal light imaging based on the automatic acquisition during the special light observation. First, the endoscope apparatus 24 sets the illumination light by the light source unit 152 to the special light (step S1). Next, the endoscope apparatus 24 starts continuous imaging by the imaging element 123, and starts inputting the continuous captured image data obtained by continuous imaging to the image processing device 23 (step S2). The captured image data is the captured image data obtained by imaging in a state in which the irradiation with the special light is performed.

In addition, the image processing device 23 starts the back-end AI analysis described above based on the captured image data from the endoscope apparatus 24 (step S3).

Next, it is assumed that the image processing device 23 detects the specific finding based on the captured image data from the endoscope apparatus 24 (step S4). In this case, the image processing device 23 stops the back-end AI analysis (step S5) and generates the still image (special light) based on the captured image data in which the specific finding is detected (step S6).

Next, the image processing device 23 transmits a detection signal indicating that the specific finding is detected to the endoscope apparatus 24 (step S7). In response to this, the endoscope apparatus 24 sets the illumination light by the light source unit 152 to the normal light (for example, the white light) (step S8).

Next, the endoscope apparatus 24 inputs the captured image data obtained by imaging by the imaging element 123 to the image processing device 23 (step S9). The captured image data is the captured image data obtained by imaging in a state in which the irradiation with the normal light is performed.

Next, the image processing device 23 generates the still image (normal light) based on the captured image data input from the endoscope apparatus 24 (step S10).

Next, the endoscope apparatus 24 sets the illumination light by the light source unit 152 to the special light (step S11). Next, the endoscope apparatus 24 starts continuous imaging by the imaging element 123 again, and starts inputting the continuous captured image data obtained by continuous imaging to the image processing device 23 (step S12). The captured image data is the captured image data obtained by imaging in a state in which the irradiation with the special light is performed.

In addition, the image processing device 23 starts the back-end AI analysis described above again based on the captured image data from the endoscope apparatus 24 (step S13). Thereafter, in a case in which the specific finding is detected again in the image processing device 23, steps S5 to S12 are repeated.

In the processing shown in FIG. 12, the image processing device 23 accumulates the still image of the normal light generated in step S10 in the medical image storage system 40 as the second still image described above.

As described above, in a case in which the still image is automatically acquired by the back-end AI analysis during the special light observation, in conjunction with the acquisition, the still image of the normal light for the report can be simultaneously captured and recorded without the switching operation by the operator of the endoscope apparatus 24.

As a result, the switching operation of the illumination light by the operator of the endoscope apparatus 24 is no longer needed, and an operation load or the troublesome operation can be reduced. In addition, since the switching operation of the illumination light does not intervene, the still image of the normal light is obtained at almost the same timing as when the special light is imaged, and thus the still image of the special light and the still image of the normal light for the same scene can be obtained. In addition, the operator of the endoscope apparatus 24 can focus on the examination or the diagnosis without considering the recording of the report and the still image.

In the example shown in FIG. 12, in steps S8 to S10, the processing of transmitting the captured image data of the normal light by the endoscope apparatus 24 to the image processing device 23 to generate the still image of the normal light by the image processing device 23 based on the captured image data has been described, but the processing is not limited to this processing. For example, processing of generating the still image of the normal light by the endoscope apparatus 24 based on the captured image data of the normal light to transmit the generated still image of the normal light to the image processing device 23 may be adopted.

In addition, the processing of stopping the back-end AI analysis in a case in which the image processing device 23 detects processing specific finding based on the captured image data has been described, but the image processing device 23 may continue the back-end AI analysis in a case in which the specific finding is detected.

Modification Example

As the use of the selected still image, the key image inserted into the report created for the examination by the endoscope has been described, but the use of the selected still image is not limited to this, and can be various uses.

In addition, although the calculation of the correct diagnosis rate has been described as an example of the back-end AI analysis, the back-end AI analysis is not limited to this, and the back-end AI analysis can be various analyses that can detect the specific finding. In addition, although the analysis using the AI has been described as the analysis for automatically acquiring the still image, the analysis for automatically acquiring the still image may be performed based on a specific algorithm that does not use the AI.

In addition, the configuration in which the first still image and the second still image are accumulated in the medical image storage system 40, but a configuration may be adopted in which the first still image and the second still image are accumulated in the endoscope department server 21, the client PC 22, or the image processing device 23.

In addition, as an example of displaying the first still image and the third still image in a comparable manner, simultaneously displaying the first still image and the third still image in different regions of the display unit 22b has been described in FIG. 9, but the control unit 22e of the client PC 22 may display the first still image and the third still image in a comparable manner by displaying the first still image and the third still image on the display unit 22b while switching between the first still image and the third still image based on time.

As described above, in the present specification, the following matters are disclosed.

(1)

An image selection support device that supports selection of a still image based on captured image data obtained by an endoscope, the device comprising a processor, and a memory, in which the memory records a first still image acquired based on the captured image data at a time when an operator of the endoscope performs an acquisition operation of a still image, and one or more second still images acquired from the captured image data at a time different from the time when the acquisition operation is performed, and the processor extracts a third still image having an imaging time point that satisfies a predetermined condition with an imaging time point of the first still image from among the one or more second still images, and associates the first still image with the third still image.

(2)

The image selection support device according to (1), in which the processor displays the first still image and the third still image on a display in association with each other.

(3)

The image selection support device according to (2), in which the processor displays the first still image and the third still image on the display in a comparable manner.

(4)

The image selection support device according to (2) or (3), in which the processor simultaneously displays the first still image and the third still image in different regions of the display.

(5)

The image selection support device according to (2) or (3), in which the processor displays the first still image and the third still image on the display while switching between the first still image and the third still image based on time.

(6)

The image selection support device according to any one of claims (2) to (5), in which the processor selects, as a selected still image, a still image for which a selection operation by a user is performed, from the first still image and the third still image displayed on the display in association with each other.

(7)

The image selection support device according to any one of (2) to (6), in which the processor extracts a fourth still image having an imaging time point that does not satisfy the condition with the imaging time point of the first still image from among the one or more second still images, displays the fourth still image on the display, and selects, as a selected still image, a still image for which a selection operation by a user is performed, from the fourth still image.

(8)

The image selection support device according to (6) or (7), in which the selected still image is a candidate image for an image to be inserted into a report of an examination by the endoscope.

(9)

The image selection support device according to any one of (1) to (8), in which the second still image is a still image acquired from the captured image data in response to a detection of a specific finding based on an analysis of the captured image data.

(10)

The image selection support device according to (9), in which the analysis includes a calculation of a correct diagnosis rate, which is a probability that a correct diagnosis is performed by the second still image, based on the captured image data, and the second still image is a still image acquired from the captured image data in a case in which the captured image data of which the calculated correct diagnosis rate is equal to or more than a certain value is continuously obtained by a certain number or more.

(11)

The image selection support device according to (9) or (10), in which the analysis is performed by an analysis device that receives the captured image data from the endoscope, and the second still image is a still image acquired from the captured image data by the analysis device.

(12)

The image selection support device according to any one of (9) to (11), in which the second still image includes a still image acquired from the captured image data obtained by the endoscope in a state in which an emission spectrum of illumination light used in imaging by the endoscope is switched in response to the detection of the specific finding based on the analysis of the captured image data.

(13)

The image selection support device according to (12), in which the second still image includes a still image acquired from the captured image data in which the specific finding is detected, and a still image acquired from the captured image data obtained by the endoscope in a state in which the emission spectrum of the illumination light used in imaging by the endoscope is switched in response to the detection of the specific finding.

(14)

The image selection support device according to any one of (1) to (13), in which the processor extracts the third still image having an imaging time point of which a difference from an imaging time point of the first still image is equal to or less than a prescribed value, from among the one or more second still images.

(15)

The image selection support device according to any one of (1) to (14), in which, in a case in which a plurality of the first still images are acquired, the processor extracts the third still image for a first still image for which a selection operation by a user is performed, from among the acquired first still images.

(16)

An image selection support method of supporting selection of a still image based on captured image data obtained by an endoscope, the method comprising, by using a first still image acquired based on the captured image data at a time when an operator of the endoscope performs an acquisition operation of a still image, and one or more second still images acquired from the captured image data at a time different from the time when the acquisition operation is performed, extracting a third still image having an imaging time point that satisfies a predetermined condition with an imaging time point of the first still image from among the one or more second still images, and associating the first still image with the third still image.

(17)

An image selection support program of supporting selection of a still image based on captured image data obtained by an endoscope, the program causing a computer to execute a process comprising, by using a first still image acquired based on the captured image data at a time when an operator of the endoscope performs an acquisition operation of a still image, and one or more second still images acquired from the captured image data at a time different from the time when the acquisition operation is performed, extracting a third still image having an imaging time point that satisfies a predetermined condition with an imaging time point of the first still image from among the one or more second still images, and associating the first still image with the third still image.

Various embodiments have been described above with reference to the drawings, but it is needless to say that the present invention is not limited to this. It is obvious that those skilled in the art can conceive various change examples or modification examples within the scope described in the claims, and naturally, such change examples or modification examples also belong to the technical scope of the present invention. In addition, the components in the embodiments described above may be optionally combined without departing from the gist of the invention.

It should be noted that the present application is based on Japanese Patent Application filed on Mar. 3, 2020 (JP2020-036270), the contents of which are incorporated herein by reference.

EXPLANATION OF REFERENCES

1: endoscope
4: control device
5: light source device
6, 22a: input unit
7: display device
10: HIS
10A: flexible part
10B: bendable part
10C: distal end part
11: operating part
12: angle knob
13: universal cord
13A: connector portion
13B: connector portion
20: endoscope department system
20A: reception
20B: pretreatment room
20C: examination room
20D: washing room
20E: conference room
21: endoscope department server
22: client PC
22b: display unit
22c: recording unit
22d: transmission/reception unit
22e: control unit
23: image processing device
24: endoscope apparatus
25: washing management device
26: washing machine
27: in-department LAN
30: pathology department system
40: medical image storage system
41, 126: communication I/F
42: signal processing unit
43: display controller
44: system control unit
45: recording medium
50: different-department system
51, 52: manually acquired image
53 to 57: automatically acquired image
60: in-hospital LAN
80: captured image data group
81: captured image data
110: insertion part
121: objective lens
122: lens group
123: imaging element
125: memory
127: imaging driving unit 150: illumination lens
151: light source processor
152: light source unit
152*a*: V-LED
152*b*: B-LED
152*c*: G-LED
152*d*: R-LED
153: light guide
154: optical path coupling unit
D1: thick frame

What is claimed is:

1. An image selection support device that supports selection of a still image, the device comprising:
an endoscope that captures image data;
a processor; and
a memory,
wherein
the memory records a first still image acquired based on the captured image data at a time when an operator of the endoscope performs an acquisition operation of a still image, and one or more second still images acquired from the captured image data at a time different from the time when the acquisition operation is performed so that the first still image does not include an image identical to the second still image,
the second still image is a still image acquired from the captured image data in response to a detection of a specific finding based on an analysis of the captured image data,
the analysis includes a calculation of a correct diagnosis rate indicating a probability that a correct diagnosis is performed based on the second still image, based on the captured image data, and
the second still image is a still image acquired from the captured image data in a case in which the captured image data of which the calculated correct diagnosis rate is equal to or more than a certain value is continuously obtained by a certain number or more, and
the processor is configured to
extract a third still image from among the one or more second still images, an imaging time point of the third still image and an imaging time point of the first still image satisfying a predetermined condition,
associate the first still image with the third still image,
display the first still image and the third still image on a display in association with each other, and
select, as a selected still image, a still image on which a selection operation by a user is performed, from the first still image and the third still image displayed on the display in association with each other.

2. The image selection support device according to claim 1,
wherein the processor displays the first still image and the third still image on the display in a comparable manner.

3. The image selection support device according to claim 1,
wherein the processor simultaneously displays the first still image and the third still image in different regions of the display.

4. The image selection support device according to claim 1,
wherein the processor displays the first still image and the third still image on the display in a switching manner based on time.

5. The image selection support device according to claim 1,
wherein the processor
extracts a fourth still image from among the one or more second still images, an imaging time point of the fourth still image and the imaging time point of the first still image not satisfying the predetermined condition,
displays the fourth still image on the display, and
selects, as a selected still image, a still image on which a selection operation by a user is performed, from the fourth still image.

6. The image selection support device according to claim 1,
wherein the selected still image is a candidate image for an image to be inserted into a report of an examination by the endoscope.

7. The image selection support device according to claim 1,
wherein the analysis is performed by an analysis device that receives the captured image data from the endoscope, and
the second still image is a still image acquired by the analysis device from the captured image data.

8. The image selection support device according to claim 1,
wherein the second still image includes a still image acquired from the captured image data obtained by the endoscope in a state in which an emission spectrum of illumination light used in imaging by the endoscope is switched in response to the detection of the specific finding based on the analysis of the captured image data.

9. The image selection support device according to claim 8,
wherein the second still image includes a still image acquired from the captured image data in which the specific finding is detected, and a still image acquired from the captured image data obtained by the endoscope in a state in which the emission spectrum of the illumination light used in the imaging by the endoscope is switched in response to the detection of the specific finding.

10. The image selection support device according to claim 1,
wherein the processor extracts the third still image from among the one or more second still images such that a difference between an imaging time point of the third still image and an imaging time point of the first still image is equal to or less than a prescribed value.

11. The image selection support device according to claim 1,
wherein, in a case in which a plurality of first still images are acquired, the processor extracts the third still image for a first still image on which a selection operation by a user is performed, from among the plurality of first still images acquired.

12. An image selection support device that supports selection of a still image, the device comprising:
an endoscope that captures image data;
a processor; and
a memory,
wherein the memory records a first still image acquired based on the captured image data at a time when an operator of the endoscope performs an acquisition operation of a still image, and one or more second still images acquired from the captured image data at a time different from the time when the acquisition operation is performed so that the first still image does not include an image identical to the second still image, and the processor is configured to extract a third still image from among the one or more second still images, an imaging time point of the third still image and an imaging time point of the first still image satisfying a predetermined condition, associate the first still image with the third still image, display the first still image and the third still image on a display in association with each other, and select, as a selected still image, a still image on which a selection operation by a user is performed, from the first still image and the third still image displayed on the display in association with each other, wherein the second still image is a still image acquired from the captured image data in response to a detection of a specific finding based on an analysis of the captured image data, the analysis includes a calculation of a correct diagnosis rate indicating a probability that a correct diagnosis is performed based on the second still image, based on the captured image data, and the second still image is a still image acquired from the captured image data in a case in which the captured image data of which the calculated correct diagnosis rate is equal to or more than a certain value is continuously obtained by six frames or more.

* * * * *